(12) United States Patent
Smith et al.

(10) Patent No.: US 8,132,911 B2
(45) Date of Patent: Mar. 13, 2012

(54) FUNDUS PHOTO-STIMULATION SYSTEM AND METHOD

(75) Inventors: Paul D. Smith, Annapolis, MD (US); Francisco de Monasterio, Bethesda, MD (US); Edward Wellner, Fairfax, VA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 305 days.

(21) Appl. No.: 12/180,877

(22) Filed: Jul. 28, 2008

(65) Prior Publication Data
US 2009/0201467 A1    Aug. 13, 2009

Related U.S. Application Data

(60) Provisional application No. 60/935,107, filed on Jul. 26, 2007.

(51) Int. Cl.
*A61B 3/14* (2006.01)
*A61B 3/10* (2006.01)

(52) U.S. Cl. ......... 351/206; 351/211; 351/214; 351/221
(58) Field of Classification Search .................. 351/200, 351/205–206, 210–211, 221, 246
See application file for complete search history.

(56) References Cited

U.S. PATENT DOCUMENTS

| | | | |
|---|---|---|---|
| 4,102,563 A | 7/1978 | Matsumura et al. | |
| 4,968,130 A * | 11/1990 | Hideshima et al. | 351/221 |
| 5,382,987 A | 1/1995 | Sperling | |
| 6,198,532 B1 | 3/2001 | Cabib et al. | |
| 2002/0036750 A1 * | 3/2002 | Eberl et al. | 351/207 |
| 2003/0179344 A1 * | 9/2003 | Van de Velde | 351/200 |
| 2004/0075812 A1 | 4/2004 | Kardon et al. | |
| 2005/0122476 A1 * | 6/2005 | Suzuki | 351/222 |
| 2006/0114411 A1 | 6/2006 | Wei et al. | |
| 2008/0111970 A1 * | 5/2008 | Kakuuchi et al. | 351/206 |

OTHER PUBLICATIONS

Gerald Westheimer, "The MaxWellian View", Neurosensory Laboratory, School of Optometry, University of California, Berkeley, CA, Vision Res., vol. 6, (Feb. 1996) pp. 669-682.
Kaija Polak, Leopold Schmetterer, and Charles E. Riva, "Influence of Flicker Frequency on Flicker-Induced changes of Retinal Vessel Diameter", Investigative Ophthalmology & Visual Science, Aug. 2002, vol. 43, No. 8 (2 pgs).
E.T. Schmeisser, J.M. Harrison, E.E. Sutter, J. Kiel, W.R. Elliott & W.E. Sponsel, "Modification of the Heidelberg Retinal Flowmeter to Record Pattern and Flicker Induced Blood flow Changes", University of Texas Health Science Center, Dept. of Opthalmology; Smith-Kettlewell Institute of Visual Sciences, Veridian, Inc., 2003, pp. 257-263.
M.A. Bearse, E.E. Sutter, "Imaging Localized Retinal Dysfunction with the Multifocal Elecroretinogram", Journal of the Optical Society of America. A, Optics, Image Science, and Vision, vol. 13, Issue 3, Mar. 1996, pp. 634-640.

* cited by examiner

*Primary Examiner* — Dawayne A Pinkney
(74) *Attorney, Agent, or Firm* — Edwards Wildman Palmer LLP; Peter F. Corless; Lisa Swiszcz

(57) ABSTRACT

An eye examination device has a fundus observation system and an optical stimulation system. The optical stimulation system has an optical targeting subsystem and an optical stimulation subsystem, wherein the optical stimulation system is structured to be used to provide light stimulation to a portion of a fundus of an eye targeted by the optical targeting subsystem in conjunction with observations made with the fundus observation system.

28 Claims, 8 Drawing Sheets

FUNDUS PHOTO-STIMULATION SYSTEM AND METHOD

CROSS REFERENCE TO RELATED APPLICATIONS

This application claims priority to U.S. Provisional Application No. 60/935,107, filed Jul. 26, 2007 the entire contents of which are hereby incorporated by reference.

BACKGROUND

1. Field of Invention

The present invention relates to optical systems and methods, and more particularly to optical systems and methods to photo-stimulate selected portions of the fundus of an eye.

2. Discussion of Related Art

Instruments are available to view and photograph the fundus of a patient's eye. For example, one such instrument in wide use is a fundus camera. FIG. 1 is an example of a conventional fundus camera 100. The fundus camera 100 is one example of an optical system to observe the fundus 102 of a subject's eye 104. The fundus camera 100 has an illumination path 106 and a viewing path 108. A constant illumination may be provided by an incandescence light bulb 110, for example. A brighter flash illumination may be provided by flash bulb 112 for use in conjunction with film-based cameras. Furthermore, the viewing path 108 may be split into a path for direct viewing 114 by a user and a path 116 to a camera 118 for photographing an image of the fundus 102 of the subject's eye 104. The beam splitter 120 may be replaced with a movable mirror 122 in some fundus cameras. The commercial fundus camera 100 is shown as an example and not meant to limit the scope of the current invention.

It is also often desirable to observe or measure subjective or objective responses of the eye or visual system as the fundus undergoes photo-stimulation and more particularly, it is often desirable to observe responses of the eye as selected portions of the fundus undergoes photo-stimulation. Such local photo-stimulation systems that can be used in conjunction with readily available fundus-observation systems such as a fundus camera are not currently available. There is thus a need for improved fundus photo-stimulation devices and methods.

SUMMARY

An eye examination device according to an embodiment of the current invention has a fundus observation system and an optical stimulation system. The optical stimulation system has an optical targeting subsystem and an optical stimulation subsystem, wherein the optical stimulation system is structured to be used to provide light stimulation to a portion of a fundus of an eye targeted by the optical targeting subsystem in conjunction with observations made with the fundus observation system.

An optical device for use with an eye observation system according to an embodiment of the current invention in which the eye observation system has an observation optical path, has a targeting light source arranged to transmit targeting light along an illumination optical path, and a stimulating light source arranged to transmit stimulating light along the illumination optical path. The optical device is structured to be used to stimulate with stimulating light a targeted portion of a fundus of an eye under observation with the eye observation system.

A method of examining a subject's eye according to an embodiment of the current invention includes illuminating a localized region of the subject's eye with targeting light, observing the localized region of the subject's eye when it is illuminated with targeting light, adjusting at least one of a position and a size of the targeting light based on the observing the localized region of the subject's eye when it is illuminated with targeting light, illuminating the localized region of the subject's eye with stimulating light, and observing a response of the subject's eye to the illuminating the localized region of the subject's eye with stimulating light.

BRIEF DESCRIPTION OF THE DRAWINGS

The invention may be better understood by reading the following detailed description with reference to the accompanying figures in which.

DETAILED DESCRIPTION

Figure 4:
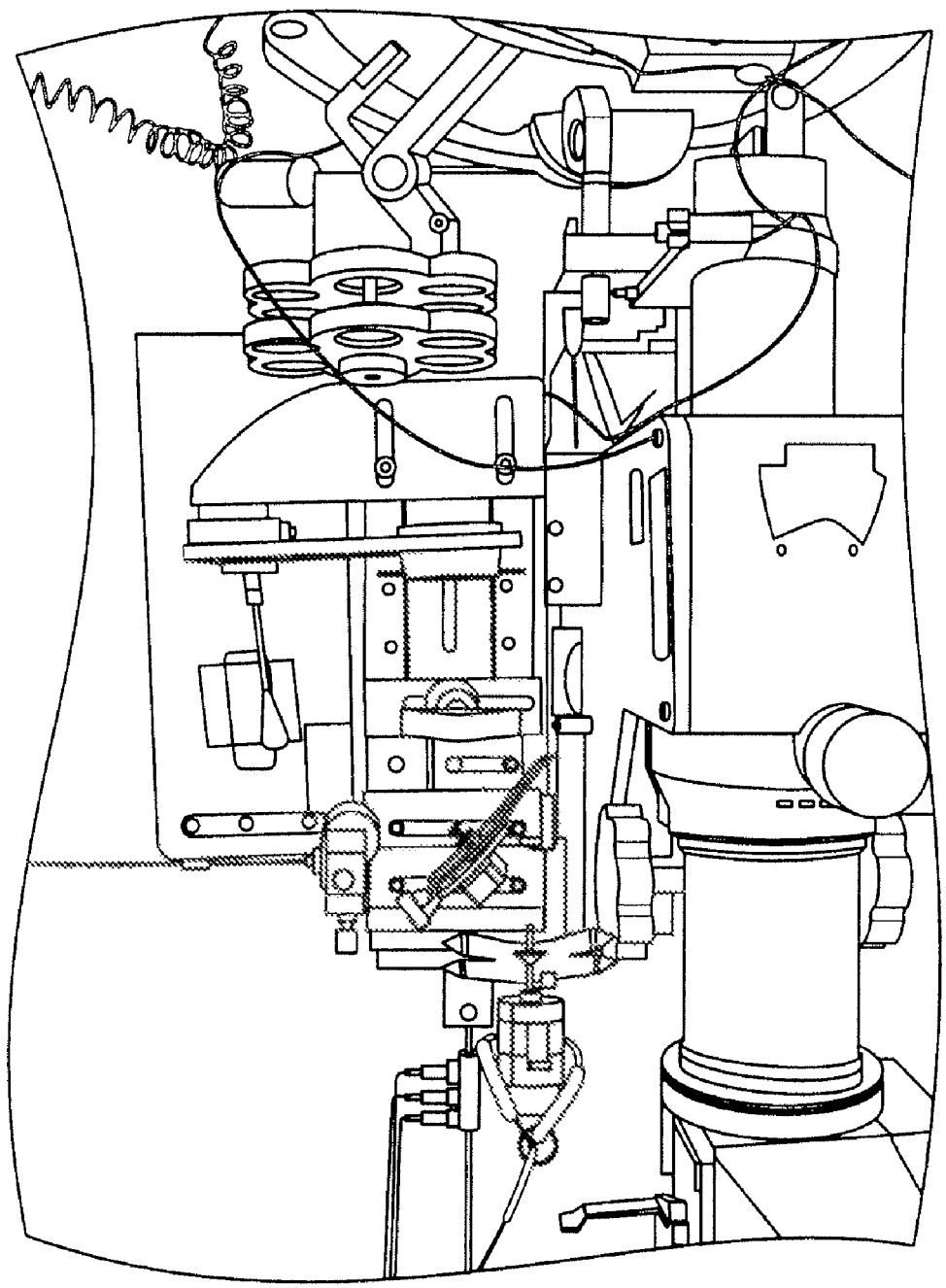
FIG. 4 is a photograph of an eye examination device according to an embodiment of the current invention in a second view.
Figure 5:
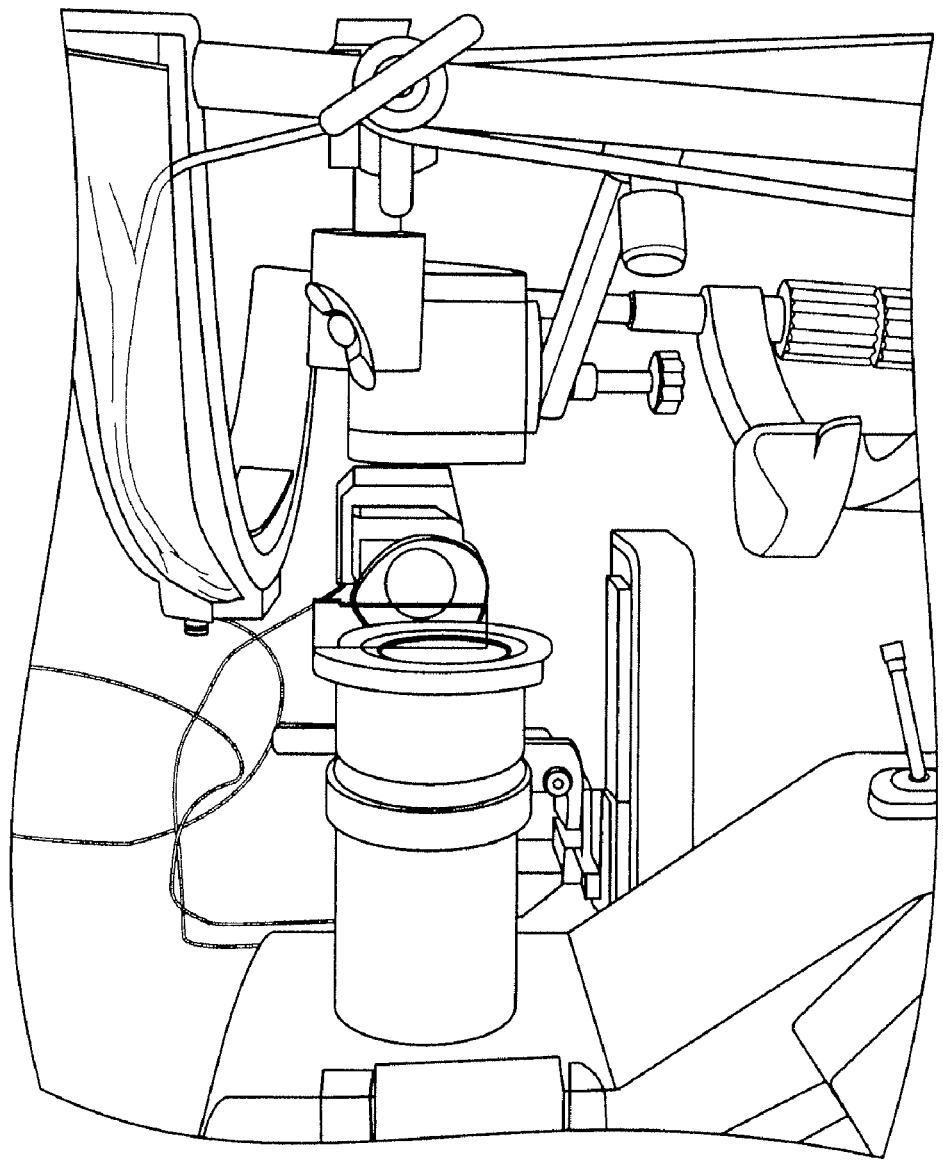
FIG. 5 is a photograph of an eye examination device according to an embodiment of the current invention in a third view.
Figure 6:
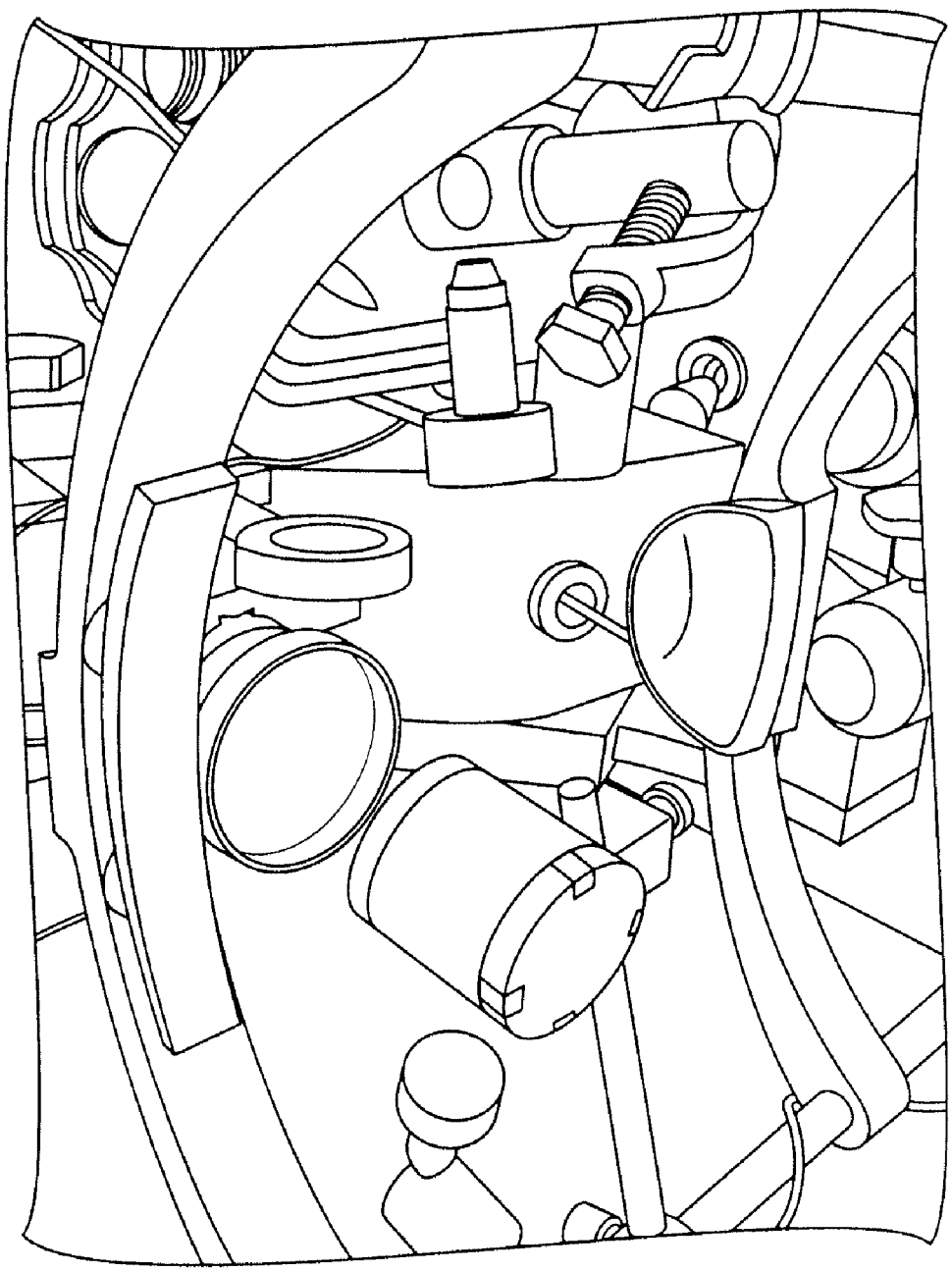
FIG. 6 is a photograph of an eye examination device according to an embodiment of the current invention in a fourth view.
Figure 7:
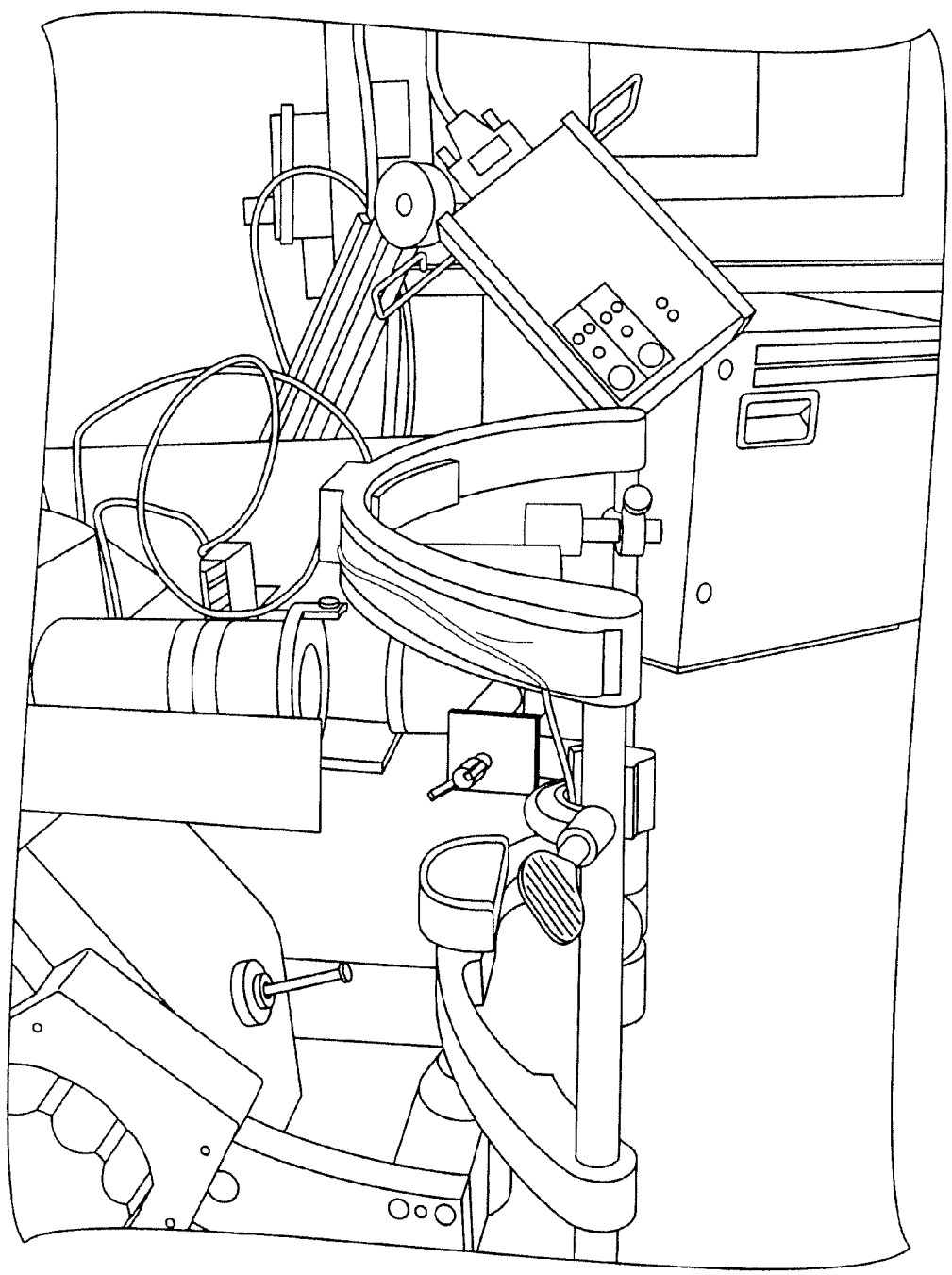
FIG. 7 is a photograph of an eye examination device according to an embodiment of the current invention in a fifth view.
Figure 8:
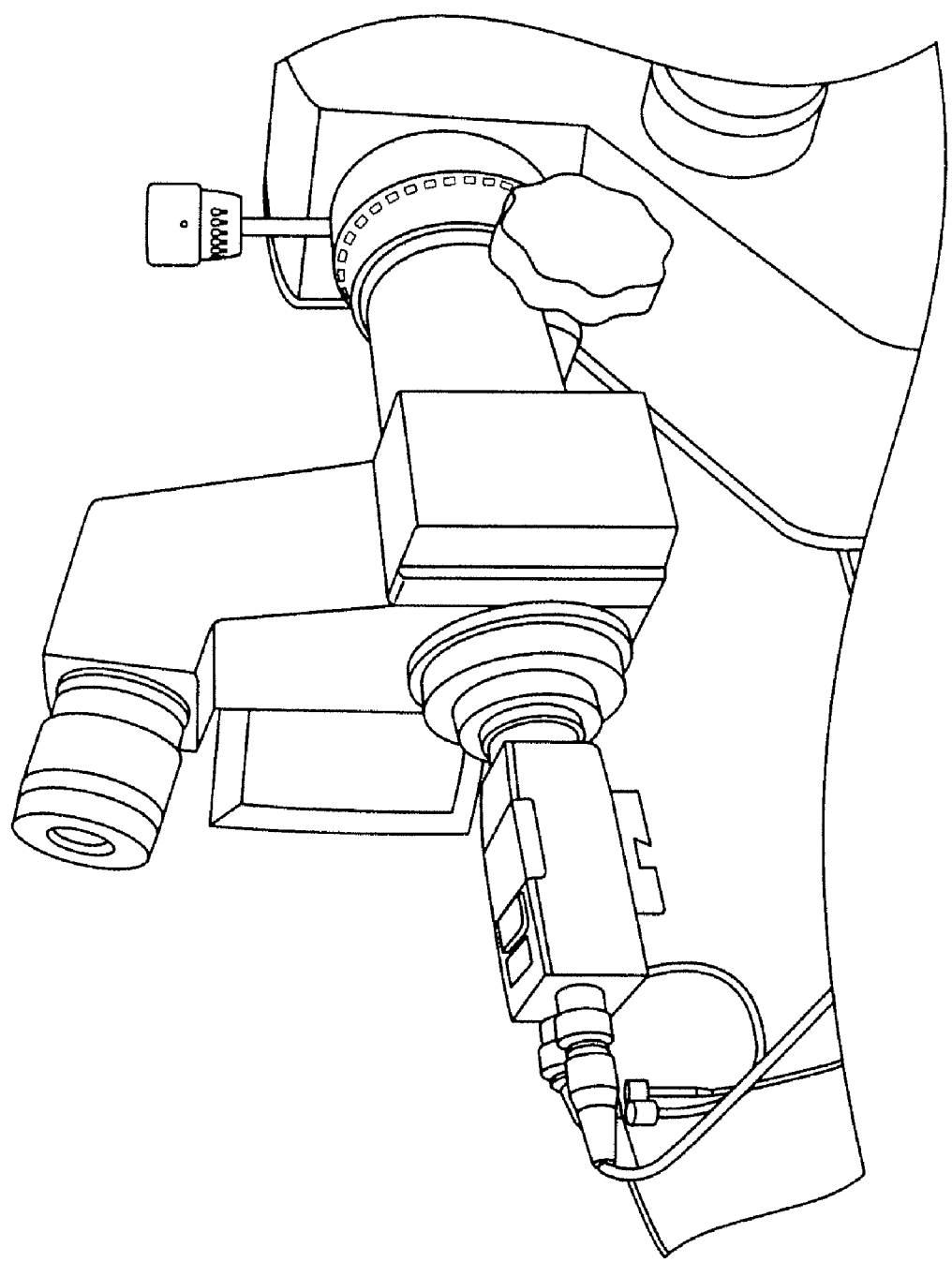
FIG. 8 is a photograph of an eye examination device according to an embodiment of the current invention in a sixth view.

An optical system according to embodiments of the current invention can be used to provide illumination of the retina using Maxwellian-view principles and providing photo-stimulation of selected regions under continuous visualization of the region being stimulated. The system can be readily integrated into commercial fundus cameras in some embodiments of the current invention, despite that such devices do not operate using Maxwellian-view optics. For example, it has been integrated with an F4 fundus camera manufactured by Zeiss in an embodiment of the current invention. Two fiber-optically coupled light systems (a targeting 670 nm laser, whose deep red output alternates on and off at 1 Hz, and a Xenon flash lamp or a 488 nm Argon laser, whose shorter wavelength output is delivered as brief flashes) are brought into co-linear alignment and arranged to enter the eye co-axially with the optical axis of the imaging fundus camera in this embodiment of the invention. The two beams are combined by means of a dichroic beam splitter, whose spectral properties are selected to maximize the intensity of the respective light beams along the optical axis, as indicated in FIG. 4. An aperture is interposed on the co-linear beams and imaged on the retina so that both the lateral position and size of the aperture can be adjusted by the operator to select the retinal area to be photo-stimulated. The optical arrangement can ensure that the stimulating flashes illuminate the same field as indicated by the deep-red targeting laser. The underlying retina and its landmarks can be seen through the fundus camera under near infrared illumination (to avoid exposing the eye to intense white-light illumination that could mask or void the responses to the flashes). For this, the incandescent light source of the camera is filtered with a near infrared bandpassfilter, and the fundus image thus obtained is observed through an adaptation to the 35 mm camera port of the fundus camera to accommodate a C-mount, infrared charge-coupled device—(CCD) camera that provides a video image of the fundus. The video image shows both the retinal fundus and, through the 670 nm targeting light, the location of the visible-light flashes and their retinal size. Eye position can be controlled by a small, dim fixation light projected through the fundus camera optics and whose position in the view field can be changed with an XY-positioner. Scattering and specular reflections originating from introduced optical elements into the external fundus camera optical path may be controlled by polarizing the targeting/photostimulation co-linear beams and crosspolarizing the observation path in the fundus camera. Fundus cameras are widely used in ophthalmology. The present invention can be used to record the electroretinogram (ERG) focally from selected, small regions of the retina to brief flashes in patients exhibiting early changes in retinal disease. The invention can permit the delivery of repeated visible-light flashes, whose size and location in the retina are controlled by a three-way adjustment of the size and location of the circular aperture, the fixation point, and the angle of the fundus camera, all under the direct visual control of the examiner.

Figure 1:
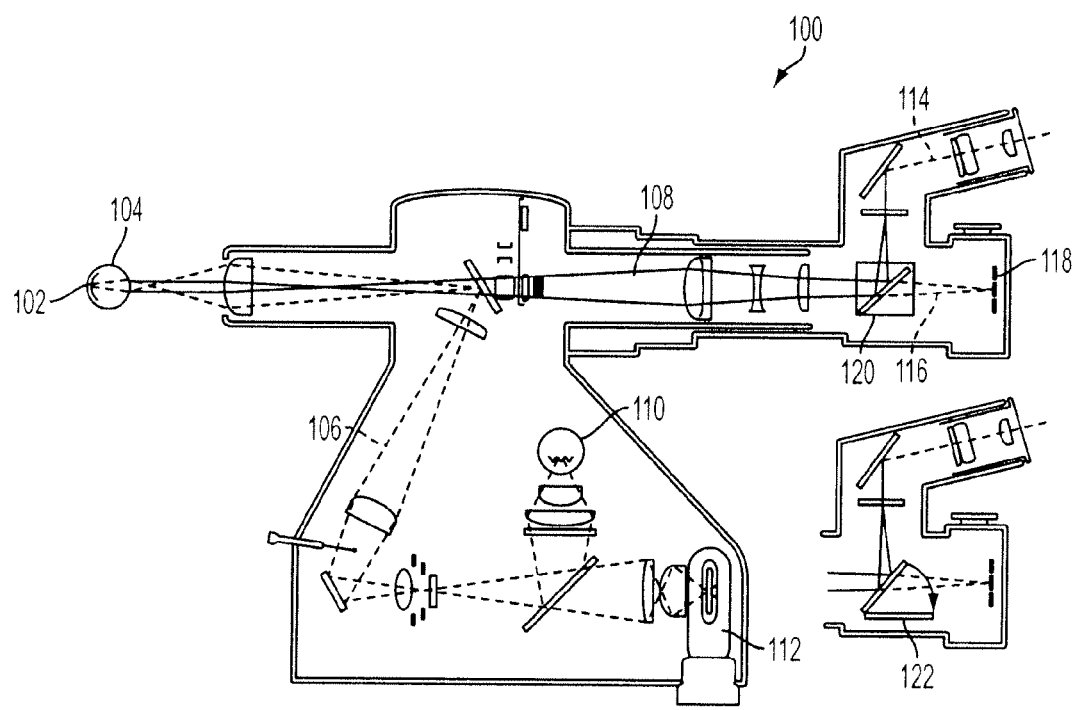
FIG. 1 is a schematic illustration of a conventional fundus camera.
Figure 2:
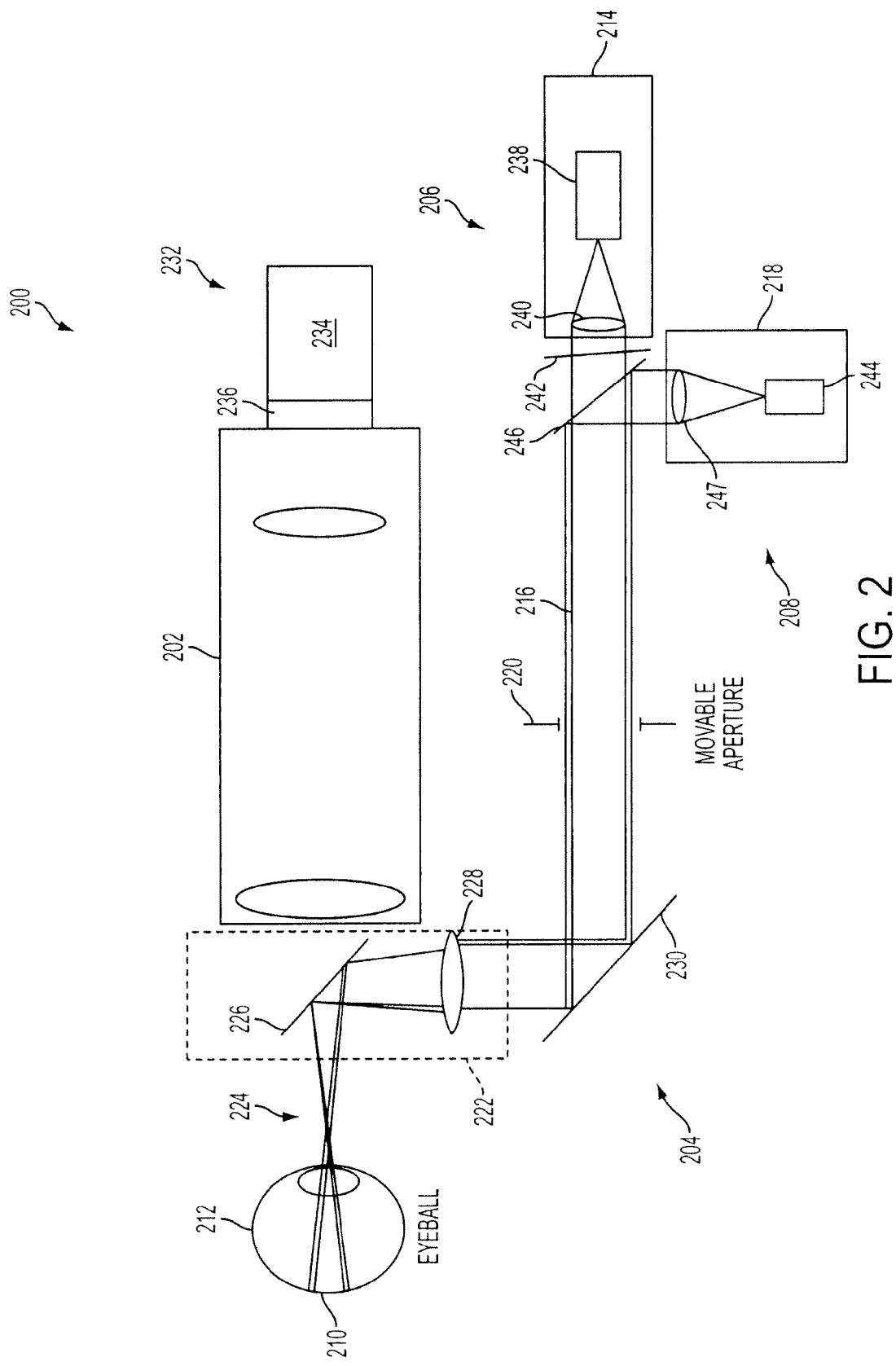
FIG. 2 is a schematic illustration of an eye examination device according to an embodiment of the current invention.
Figure 3:
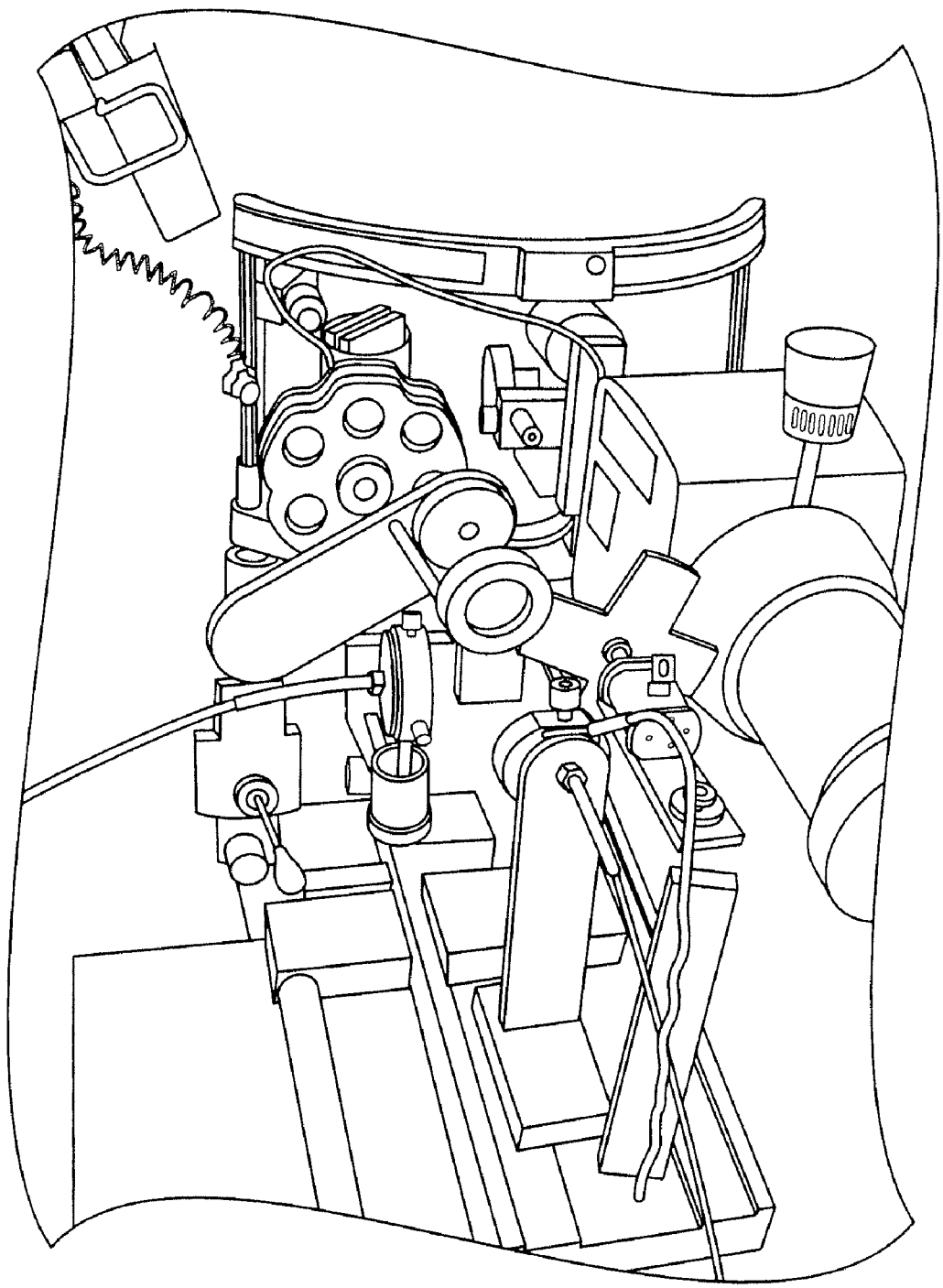
FIG. 3 is a photograph of an eye examination device according to an embodiment of the current invention in a first view.

FIG. 2 is a schematic illustration of an eye examination device 200 according to an embodiment of the current invention. The eye examination device 200 has a fundus observation system 202 and an optical stimulation system 204. The optical stimulation system 204 comprises an optical targeting subsystem 206 and an optical stimulation subsystem 208. The optical stimulation system 204 is structured to be used to provide light stimulation to a portion of a fundus 210 of an eye 212 targeted by the optical targeting subsystem 206 in conjunction with observations made with the fundus observation system 202.

The optical targeting subsystem 206 comprises a targeting light source 214 to provide targeting light along an illumination optical path 216. The optical stimulation subsystem 208 comprises a stimulating light source 218 to provide stimulating light along the illumination optical path 216. The optical stimulation system 204 includes an aperture stop 220 arranged at a position along the illumination optical path 216. The aperture stop 220 may be movable to be repositioned along the optical path 216 as well as being adjustable to adjust the aperture size. The optical stimulation system 204 comprises a front end optical system 222 that is structured and arranged to project an image of an aperture in the aperture stop 220 along at least a portion of the observation optical path 224 onto the fundus 210 of the eye 212. The front end optical system 222 may include a beam splitter 226 and an imaging lens system 228. By positioning the beam splitter 226 so that the corneal entry point of the co-linear beams of sources 214 and 218 (reflected by this beam splitter) is located within the annular entry point of the infrared fundus illumination of the fundus camera, two critical goals are achieved: First, it is possible to avoid the parasitic corneal reflection produced whenever the beams enter through the center of the cornea, which severely interferes with viewing of the fundus; second, it seamlessly combines the Maxwellian optics of the co-linear dual beam system of photo-localization and photostimulation of the present invention with the non-Maxwellian optics of the fundus camera. The imaging lens system 228 is illustrated schematically as a single lens in FIG. 2, but the concepts of the current invention are not limited to such a construction. It may be a single lens or a plurality lenses, and it can include compound lenses, refractive lenses, diffractive lenses and/or gradient index lenses, for example. The type of imaging lens system 228 may be selected as appropriate to the particular embodiment of the current invention. The lens system 228 may be structured so that it is attachable to and detachable from the fundus observation system 202. Similarly, the beam splitter 226 may be constructed so that it is attachable to and detachable from the fundus observation system 202. For example, a collar structure may be attached to the front of a conventional fundus camera, as one particular example of a fundus observation system 202, and the beam splitter 226 may be attached to the collar. A lens system 228 may be structured so it can be attached to the same collar as the beam splitter 226, or it can be attached with a separate structure. For example, it may be attachable to and detachable from the fundus observation system 202 directly. The beam splitter 226 redirects targeting and stimulating light so that it is redirected into the eye 212. At the same time, the beam splitter 226 permits observation and/or recording of images and/or data from light that passes through the beam splitter 226 into the fundus observation system 202. The imaging lens system 228 is arranged relative to the aperture stop 220 and the eye 212 such that a combined effect of the lens of the eye 212 and the imaging system 228 is to image the aperture of the aperture stop 220 onto the fundus 210 of the eye 212. In the example of FIG. 2, the illumination path 216 is folded by mirror 230.

The optical stimulation system 204 may also include a camera system 232. The camera system 232 may include a digital camera 234, for example. However, the invention is not limited to the use of only a digital camera. The digital camera may be a still camera or a video camera, or a combination of both. Furthermore, a film camera or other optical recording device may be used without departing from the general concepts of the current invention. The camera system 232 may also include a mounting component 236 that is suitable to mount a camera 234 to the fundus observation 202. For example, the camera 234 may be a digital camera that is mounted to a conventional fundus camera. The mounting component 236 may also include an optical system therein to project an appropriately sized image onto a photo-sensitive element of the camera 234.

The targeting light source 214 may include a first light source 238 to generate targeting light as well as a collimating lens system 240 to collimate targeting light produced by the first light source 238. The collimating lens system 240 may be a single lens or may be a compound lens system. Furthermore, it may include refractive, diffractive and/or gradient index lenses as is suitable for the particular application. The general concepts of the invention are not limited to the particular structure of the collimating lens. For some applications, the first light source 238 may be a source of light in the deep red end of the optical spectrum. For example, the first light source 238 may be a laser, a light emitting diode, or other suitable source of light. If desired in some applications, the first light source 238 may be optically coupled to an optical fiber or other optical waveguide. The targeting light source 214 may also include optical filters, as may be suitable for the particular application. For example, the targeting and light source 214 may include a low-pass filter or a band-pass filter to attenuate visible light having shorter wavelengths than deep red regions of the visible spectrum. The optical targeting subsystem 206 may also include a chopper 242 to cause targeting light from the targeting light source 214 to have a time-varying intensity to facilitate recognition of targeting light by a user of the eye examination device 200 in an image that includes an image of the fundus of the eye. Targeting light that varies in intensity with time can be easier to recognize by a user in a complex background image compared to a constant intensity targeting light image. One example of a suitable chopper 242 is a mechanical chopper having a rotating wheel that presents alternating blocking (or attenuating) and substantially transmitting regions to the incident beam. A frequency of around 1 cycle per second to a few cycles per second has been found to be suitable for facilitating recognition of targeting light by a human observer. However, the general concepts of the invention are not limited to requiring that there be a chopper, and are not limited to a particular type of chopper or to the specific frequency of intensity variation.

The stimulating light source 218 can include a second light source 244 and a collimating lens system 246. The collimating lens system 246 may be a single lens, a compound, a system of lenses and/or may include any combination of suitable available lens such as refractive lenses, diffractive lens and gradient index lenses. The second light source 244 may be selected to have light at a desired wavelength to have a desired stimulating effect on the eye 212. For example, the second light source 244 may be a laser or light emitting diode having a frequency in the middle of the visible spectrum, for example, in the green or blue regions of the visible spectrum. However, the broad concepts of the invention are not limited to the specific type of second light source 244 or to the specific spectral output of the light source 244. Stimulating light from the stimulating light source 218 is reflected by a reflective component 246. The reflective component 246 can be a beam splitter in one embodiment of the invention, or a dichroic mirror, for example. Alternatively, the reflective component 246 may be a substantially 100% reflective mirror which is movable into and out of the illuminating light path 216. In the case in which the reflective component 246 is a movable mirror, it can be moved out of the path of illumination light 216 to permit targeting light to pass substantially without being obstructed by the reflective component 246. Once an area for stimulation is selected with targeting light, the reflective component 246 may then be moved into a path of stimulating light to redirect the stimulating light along the illuminating path 216.

The fundus observation system 202 may be a fundus camera according to some embodiments of this invention. For example, the fundus observation system 202 may be a conventionally available fundus camera to which the optical stimulation system 204 may be attached and/or otherwise arranged to be used in conjunction therewith. For example, in some embodiments the mounting component 236 may be structured to permit one to mount the camera 234 to the camera port of an available fundus camera to provide both the structural attachment of the camera 234 as well as providing the appropriate imaging of the fundus image onto a photosensitive element of the camera 234. Similarly, the front end optical system 222 may be structured to be attachable to the end of a conventional fundus camera that is closest to the eye under observation. Therefore, in some embodiments, the optical stimulation system 204 is suitable to be used as an add-on component to an available fundus camera. However, the general concepts of this invention are not limited to only such embodiments. The eye examination device 200 may be a complete, stand-alone system in other embodiments and may include fundus observation systems other than conventionally available fundus cameras.

In operation, one can observe the fundus 210 of an eye 212 with the fundus observation system 202. The fundus observation system 202 may be, but is not limited to, a fundus camera. The fundus observation system 202 may include an illumination system to illuminate the fundus 210 of the eye 212. The fundus may be observed with the camera system 232 and/or through a direct observation eyepiece. Targeting light can be generated by the targeting light subsystem 206 to provide collimated targeting light that travels along illumination path 216 to pass through an aperture in the movable and adjustable aperture stop 220. The size and location of the transmitting aperture of the aperture stop 220 may be varied so as to illuminate a portion of the fundus 210 of the eye 212. The targeting light traveling along illumination path 216 can be redirected by folding mirror 230 in some embodiments to provide a more compact arrangement for the optical stimulation system 204. Targeting light then passes through imaging lens system 228 of the front end optical system 222 and is redirected by beam splitter 226 to direct it onto the fundus 210 of the eye 212 along a portion 224 of an imaging light path. The imaging lens system 228 in conjunction with the lens of the eye 212 form an image of the aperture of the aperture stop 220 onto the fundus 210. Depending on the size and location of the aperture of the aperture stop 220, a portion of the fundus 210 is illuminated with targeting light. Both the fundus 210 and the portion illuminated with targeting light are observed with the fundus observation system 202 as a superimposed image. The chopper 242 may be used to facilitate recognition of the targeting portion of the fundus 210. If the targeted portion of the fundus is not at the desired location and/or size, the size and position of the aperture 220 may be changed to reposition the desired portion of the fundus 210. Upon targeting the desired portion of the fundus 210, the operator can then illuminate the targeted region with stimulating light from the stimulating light source 218. For example, in one embodiment, the reflective component 246 is a movable mirror which can be moved into position to redirect light from the stimulating light source 218 along the illumination path 216 and through the aperture of the aperture stop 220. Upon stimulating the targeted portion of the fundus 210 with stimulating light, one may then observe a responsive of the eye to the stimulating light. For example, one may obtain an ERG—in conjunction with stimulating targeted portions of the fundus 210. However, the current invention is not limited to only observing responses by means of an ERG. Other types of observations of responses of the eye to targeted stimulation—such as, but not limited to, micro-perimetry, local adaptation thresholds, small-field spectral sensitivity and other measurements which may include subjective or objective responses to the localized photo-stimulation of the retina—may be made without departing from general concepts of the current invention. Observations may also include photographs, videos or other types of observations which may include recording information and/or signals for later or additional processing.

The embodiments and particular examples described herein are intended to help explain various concepts of the invention. The invention is not intended to be limited to these particular embodiments and examples. One of ordinary skill in the art would recognize that numerous modifications and alternatives are possible within the teachings of this invention without departing from the scope of the invention, which is defined by the appended claims.

We claim:

1. An optical device for use with an eye observation system, said eye observation system having an observation optical path, said optical device comprising:
   a targeting light source arranged at a first position to transmit targeting light along an illumination optical path;

a stimulating light source arranged at a second position to transmit stimulating light along said illumination optical path; and an aperture arranged at a position along said illumination optical path such that selected portions of the targeting light and the stimulating light pass therethrough to illuminate a targeted portion of a fundus of an eye, the aperture configured to be adjustable in both lateral position and size to thereby adjust and select the targeted portion of the fundus such that the targeting light and stimulating light illuminate the same targeted portion of the fundus, wherein said optical device is structured to be used to stimulate with stimulating light the targeted portion of the fundus of the eye while under observation with said eye observation system.

2. An optical device for use with an eye observation system according to claim 1, further comprising a front-end optical system constructed and arranged to project an image of said aperture along at least a portion of said observation optical path onto said fundus.

3. An optical device for use with an eye observation system according to claim 2, wherein said front end optical system comprises a beam splitter that is attachable to, and detachable from, said eye observation system.

4. An optical device for use with an eye observation system according to claim 3, wherein said front end optical system comprises an imaging lens system that is adapted to project said image of said aperture onto said fundus.

5. An optical device for use with an eye observation system according to claim 1, further comprising a camera system that is mountable to an imaging port of said eye observation system.

6. An optical device for use with an eye observation system according to claim 5, wherein said camera system comprises an electronic camera.

7. An optical device for use with an eye observation system according to claim 6, wherein said camera system comprises a mounting component and an optical system for projecting an image from an observation onto a photo-sensitive element of said electronic camera.

8. An optical device for use with an eye observation system according to claim 1, wherein said targeting light is substantially red light at a deep red end of a visible light spectrum.

9. An optical device for use with an eye observation system according to claim 1, further comprising a chopper disposed in a targeting-light optical path, said chopper causing targeting light to have a time-varying intensity to facilitate recognition of targeting light in an image that includes an image of at least a portion of said fundus.

10. An optical device for use with an eye observation system according to claim 1, wherein said targeting light source comprises a first laser and said stimulating light source comprises a second laser.

11. An optical device for use with an eye observation system according to claim 1, wherein said eye observation system is a fundus camera.

12. An eye examination device, comprising:

a fundus observation system; and an optical stimulation system comprising an optical targeting subsystem and an optical stimulation subsystem, wherein said optical targeting subsystem is structured to be used to provide targeting light along an illumination optical path to a target portion of a fundus of an eye, wherein said optical stimulation system is structured to be used to provide stimulating light along the illumination optical path to the target portion of the fundus of the eye targeted by said optical targeting subsystem in conjunction with observations made with said fundus observation system, wherein said optical stimulation system further comprises an aperture arranged at a position along said illumination optical path, said aperture being constructed and arranged to allow selected portions of targeting and stimulating light to pass therethrough to illuminate the targeted portion of the fundus of the eye said aperture further being configured to be adjustable in both lateral position and size, and wherein the optical stimulation system is configured such that co-linear beams of targeting light and the stimulating light enter the eye within an annular entry point of illumination from the fundus observation system.

13. An eye examination device according to claim 12, wherein said optical targeting subsystem comprises a targeting light source to provide said targeting light and said optical stimulation subsystem comprises a stimulating light source to provide said stimulating light.

14. An eye examination device according to claim 12, wherein said optical stimulation system comprises a front-end optical system structured and arranged to project an image of said aperture along at least a portion of an observation optical path onto said fundus.

15. An eye examination device according to claim 14, wherein said front-end optical system comprises a beam splitter that is attachable to, and detachable from, said fundus observation system.

16. An eye examination device according to claim 15, wherein said front-end optical system comprises an imaging lens system that is adapted to project said image of said aperture onto said fundus.

17. An eye examination device according to claim 12, wherein said optical stimulation system comprises a camera system that is mountable to an imaging port of said fundus observation system.

18. An eye examination device according to claim 17, wherein said camera system comprises an electronic camera.

19. An eye examination device according to claim 18, wherein said camera system comprises a mounting component and an optical system for projecting an image from an observation onto a photo-sensitive element of said electronic camera.

20. An eye examination device according to claim 12, wherein said targeting light is substantially red light at a deep red end of a visible light spectrum.

21. An eye examination device according to claim 13, wherein said optical targeting subsystem comprises a chopper disposed in a targeting light optical path, said chopper causing targeting light to have a time-varying intensity to facilitate recognition of targeting light in an image that includes an image of at least a portion of said fundus.

22. An eye examination device according to claim 13, wherein said targeting light source comprises a first laser and said stimulating light source comprises a second laser.

23. An eye examination device according to claim 12, wherein said retina observation system is a fundus camera.

24. A method of examining a subject's eye, comprising:

illuminating a localized region of said subject's eye with targeting light, the targeting light being provided along an illumination optical path, wherein an aperture is positioned along said illumination optical path;

observing said localized region of said subject's eye when it is illuminated with targeting light;

adjusting the aperture so as to adjust at least one of a position and a size of said targeting light based on said observing said localized region of said subject's eye when it is illuminated with targeting light, thereby illuminating a select target portion of the fundus of the eye;

illuminating said localized region of said subject's eye with stimulating light, the stimulating light being provided along said illumination optical path, wherein selected portions of the stimulating light pass through the aperture to thereby illuminate the select target portion of the fundus of the eye with stimulating light; and observing a response of said subject's eye to said illuminating said localized region of said subject's eye with stimulating light.

25. A method of examining a subject's eye according to claim 24, wherein said observing a response comprises recording at least one of a signal and data corresponding to said response.

26. A method of examining a subject's eye according to claim 24, wherein said observing a response comprises recording an electroretinogram.

27. A method of examining a subject's eye according to claim 24, further comprising at least one of blocking or attenuating said targeting light at a periodic interval to facilitate recognition of targeting light during said observing said localized region of said subject's eye.

28. A method of examining a subject's eye according to claim 27, wherein said at least one of blocking or attenuating includes chopping said targeting light with an optical beam chopper.

* * * * *